United States Patent [19]
Schmidt et al.

[11] Patent Number: 6,011,041
[45] Date of Patent: Jan. 4, 2000

[54] USE OF ANHYDROVINBLASTINE

[75] Inventors: Bruce Schmidt; James Kutney, both of Vancouver; Lawrence Mayer, North Vancouver, all of Canada

[73] Assignee: University of British Columbia, Vancouver

[21] Appl. No.: 08/690,195

[22] Filed: Jul. 26, 1996

Related U.S. Application Data

[60] Provisional application No. 60/001,637, Jul. 28, 1995.

[51] Int. Cl.[7] ............... A61K 31/33; A61K 43/42; A61K 31/485; C07D 519/04
[52] U.S. Cl. ............... 514/283; 514/183; 514/908; 540/478; 540/479; 546/91
[58] Field of Search ............... 514/908, 183, 514/283; 540/478, 479; 546/51

[56] References Cited

U.S. PATENT DOCUMENTS 4,029,663  6/1977  Gutowski et al. .
4,144,237  3/1979  Kutney .
4,307,100 12/1981  Langlois et al. ............... 546/51

FOREIGN PATENT DOCUMENTS 02002  3/1988  WIPO .

OTHER PUBLICATIONS

Registry No. 38390–45–3, Jun. 26, 1997.
LeChevalier et al, Anticancer Res. vol. 12 p. 1794, 1992.
REmington's Pharmaceutical Sciences, 16 Edition, pp. 1518–1534, 1980.

*Primary Examiner*—Nancy A Johnson
*Attorney, Agent, or Firm*—Gray, Cary, Ware & Friendenrich, LLP; Lisa A. Haile

[57] ABSTRACT

The present invention is particularly directed to the use of a derivative of vinblastine, 3',4'-anhydrovinblastine (AHVB), which differs from vinblastine in that it possesses a double bond at the 3',4' position of the caranthine nucleus rather than the hydroxyl group that is present in the parent structure, as an antineoplastic agent in the therapeutic treatment of cancer. Specifically, the treatment of lymphoma with 3',4'-anhydrovinblastine is disclosed.

6 Claims, 8 Drawing Sheets

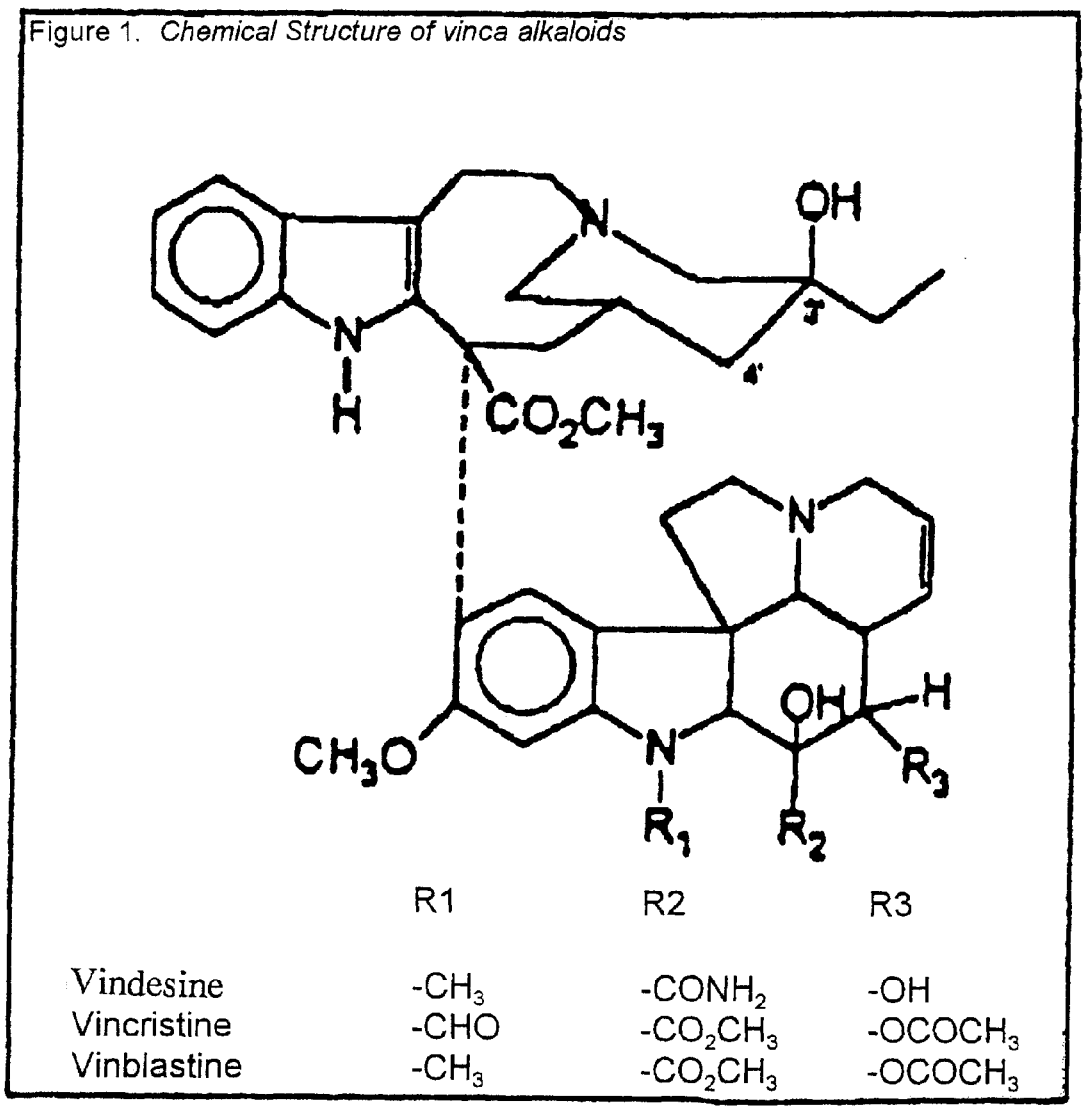
Figure 1: Chemical structure of some vinca alkaloids.

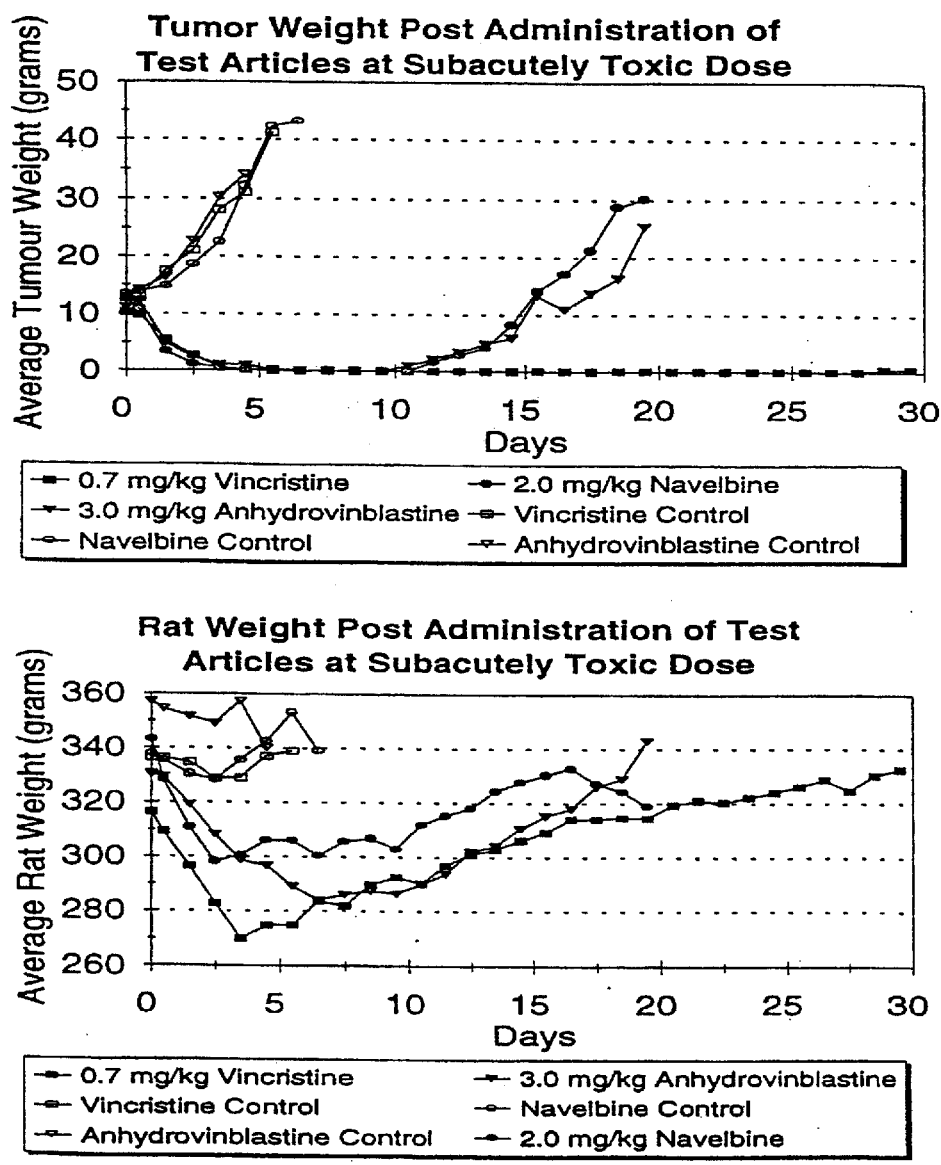

Figure 2: Comparison of the effects of administering a single intraperitoneal injection, at a subacutely toxic dose, of vincristine sulfate (0.7 mg/kg), navelbine (2.0 mg/kg) and AHVB (3.0 mg/kg) to Nb rats bearing single well-developed, subcutaneous Nb2-U17 tumor transplants on i) average tumor weight (upper panel) and ii) average weight of the rat (lower panel) as a function of time. As controls for each drug, Nb2-U17 tumor transplant-bearing rats injected with saline were used.

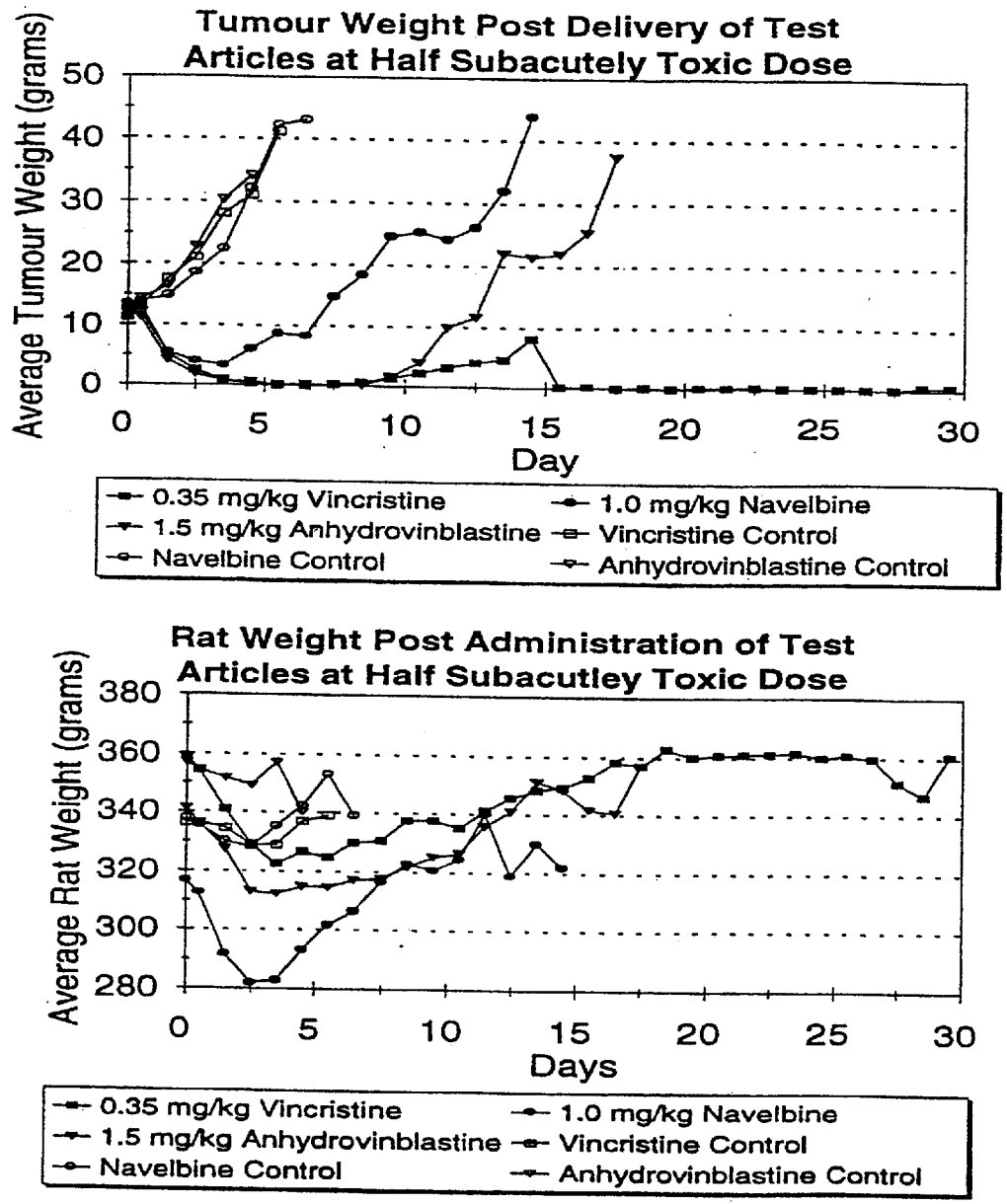

Figure 3: Comparison of the effects of administering a single intraperitoneal injection, at a half subacutely toxic dose, of vincristine sulfate (0.35 mg/kg), navelbine (1.0 mg/kg) and AHVB (1.5 mg/kg) to Nb rats bearing single well-developed, subcutaneous Nb2-U17 tumor transplants on i) average tumor weight (upper panel) and ii) average weight of the rat (lower panel) as a function of time. As controls for each drug, Nb2-U17 tumor transplant-bearing rats injected with saline were used.

Changes in Mean Animal Weight of BDF 1 Mice Bearing Intraperitoneal P388 Tumors Following i.v. Administration of Saline, Vincristine (4 mg/kg), Navelbine (40mg/kg) and Anhydrovinblastine (40mg/kg)
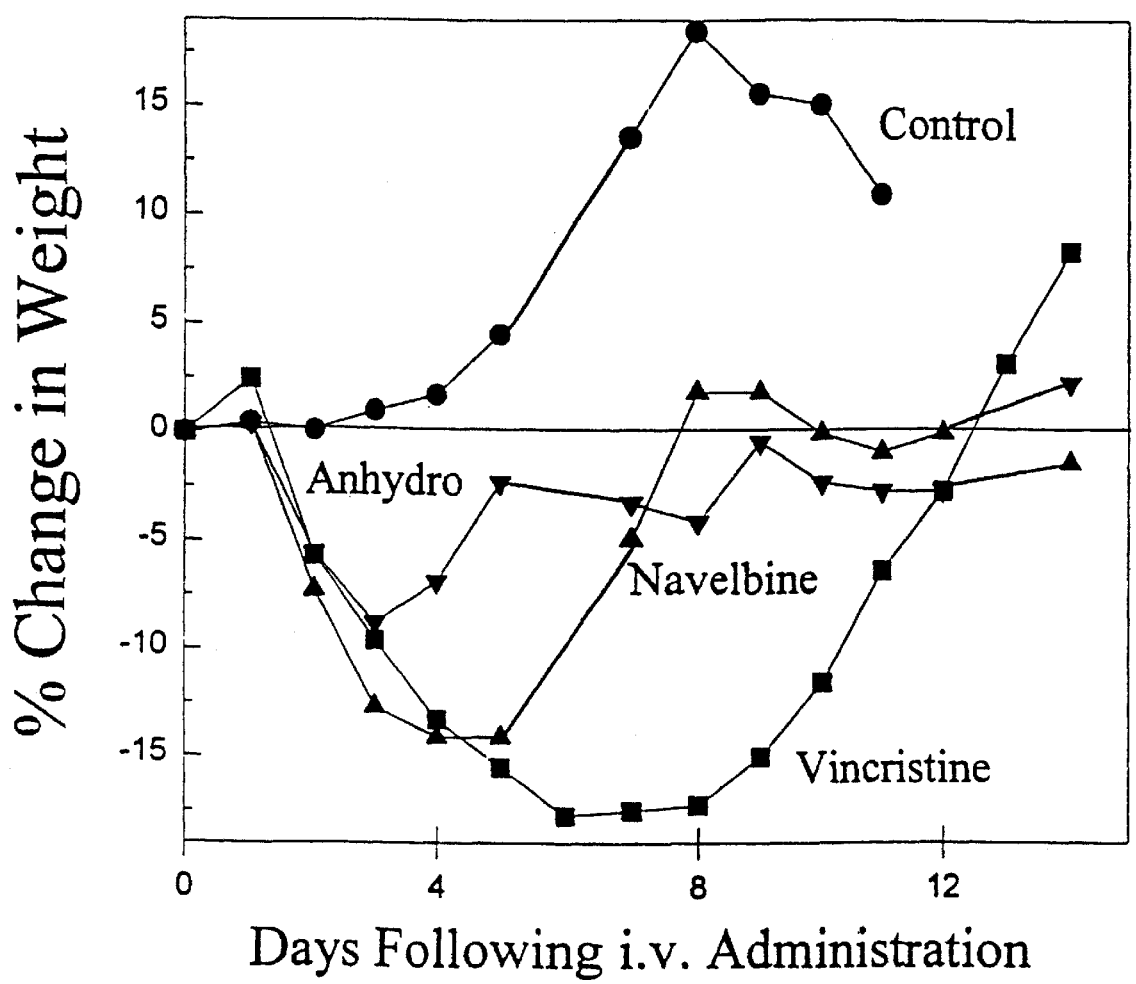
Figure 4: Vinca alkaloid induced weight loss following a single i.v. injection of the indicated drug at the maximum tolerated dose.

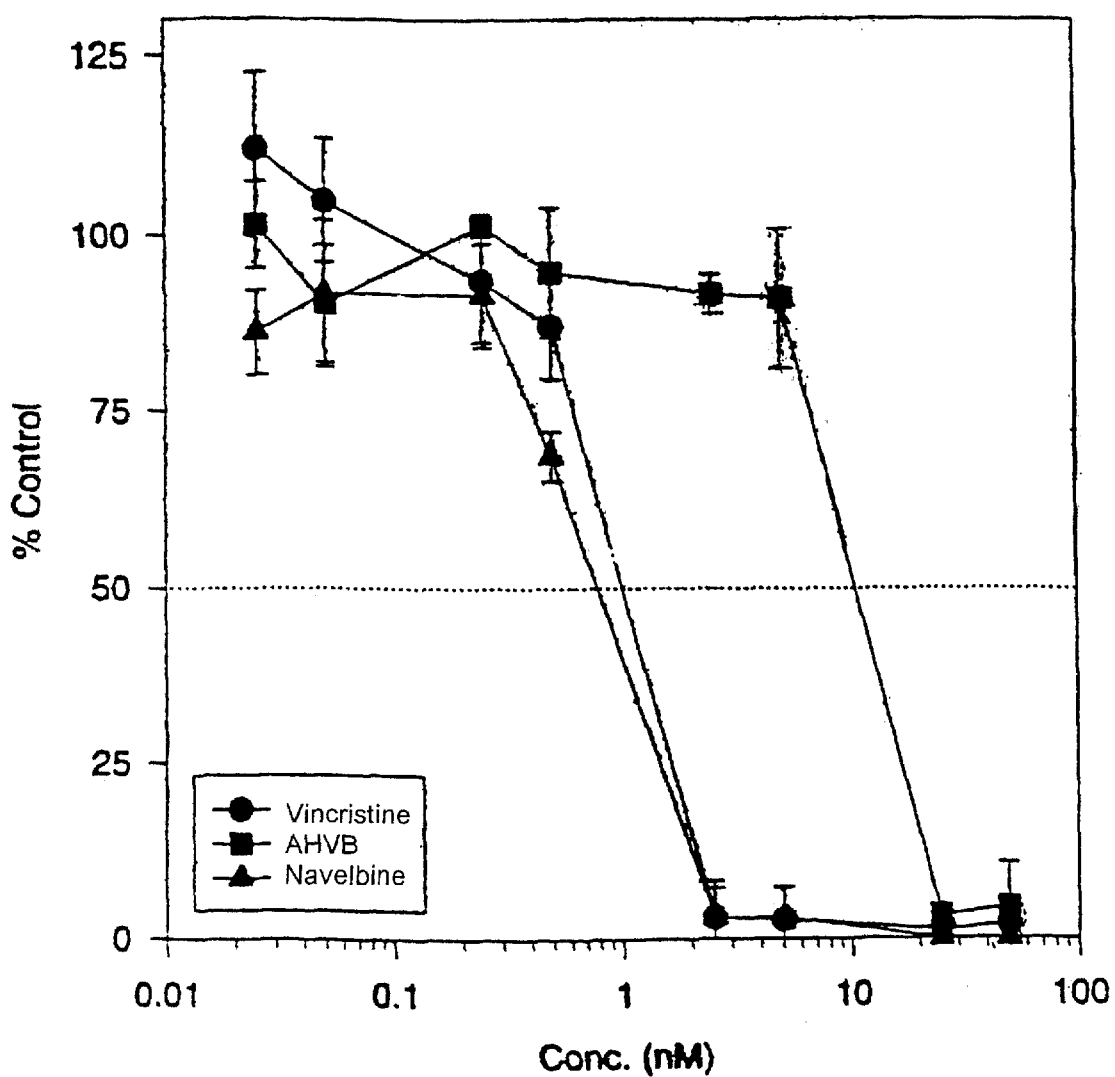
Figure 5: Example cytotoxicity curve used to estimate the $IC_{50}$ of various vinca alkaloids.

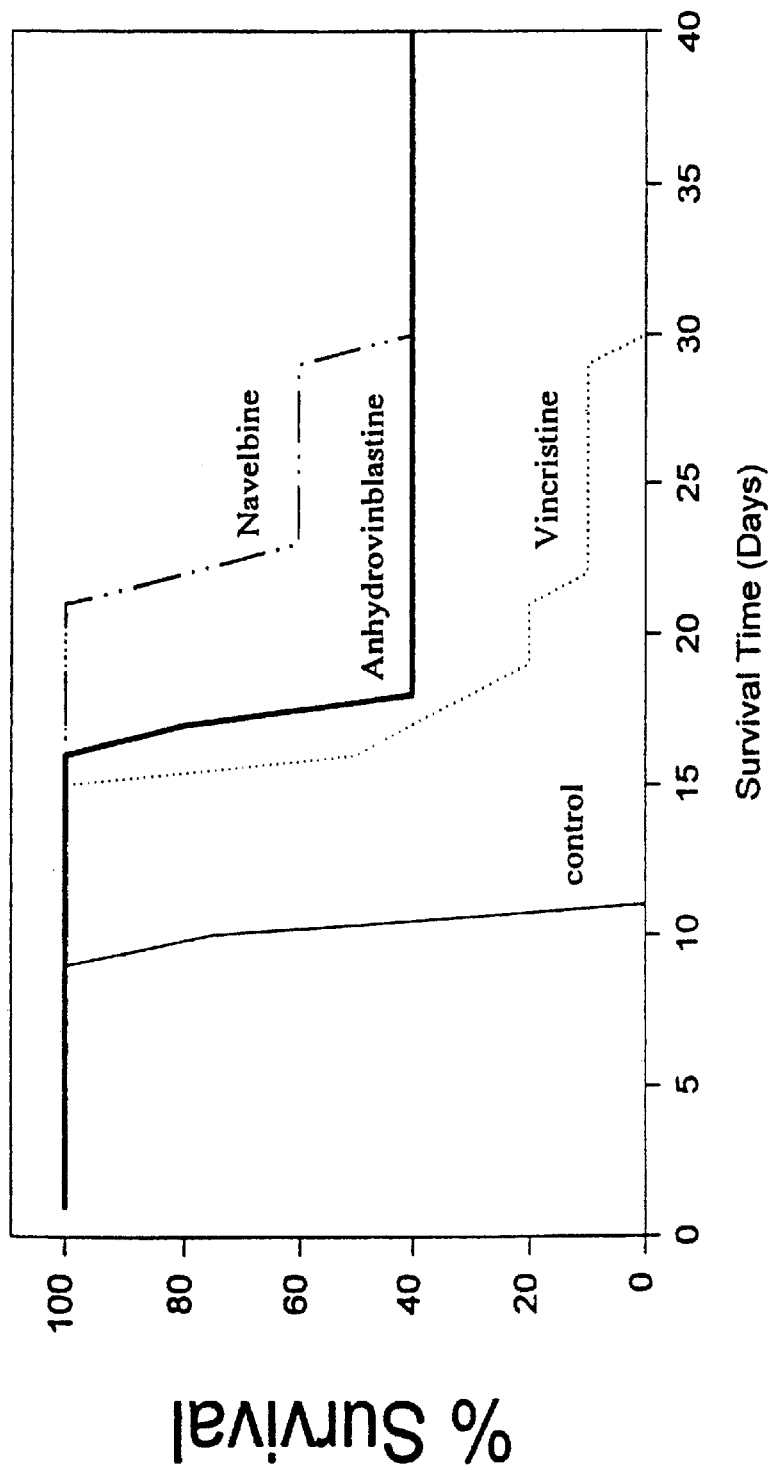
Figure 6: P388 antitumor activity of selected formulations of vinca alkaloids.

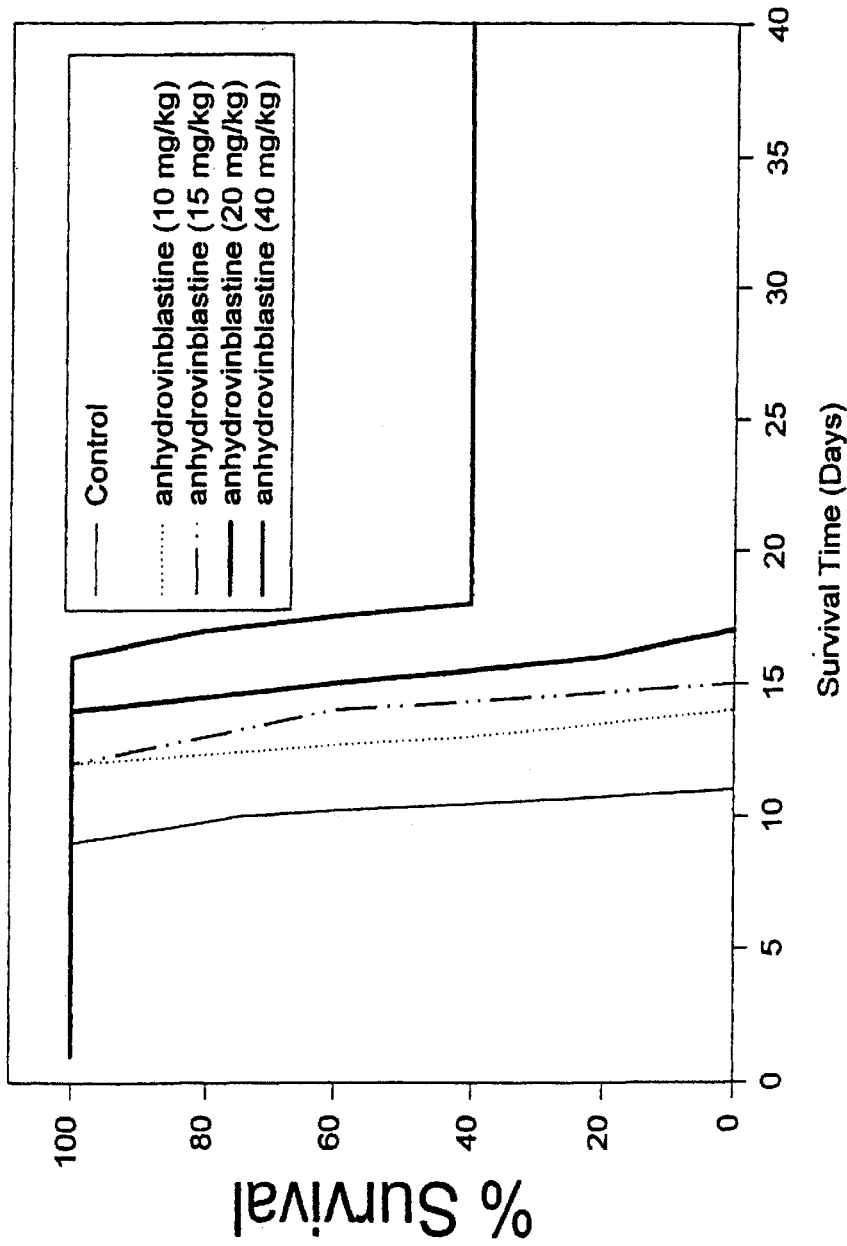
Figure 7: Dose response curve obtained for AHVB when used to treat BDF1 mice bearing P388 tumors.

USE OF ANHYDROVINBLASTINE

This application claims priority from U.S. patent application Ser. No. 60/001,637, filed Jul. 28, 1995, now abandoned, the contents of which are hereby incorporated by reference.

TECHNICAL FIELD

The present invention is related generally to the use of antineoplastic vinca alkaloids as antitumour agents. More particularly, the present invention is related to providing use for a derivative of vinblastine, anhydrovinblastine, as an antineoplastic agent with improved therapeutic properties, demonstrating a significantly higher maximum tolerated dose and less toxicity than its parent and related compounds.

BACKGROUND OF INVENTION

Due to a high degree of unpredictability, classic techniques of drug development are inventive. Mostly through a process of elimination, a large number of natural products and synthetic chemical compounds are screened for desired effects, using a series of increasingly complex systems, beginning with simple in vitro cell-level assays, progressing to animals and finally human clinical trials. But, due to essential characteristics such as adsorption, distribution and metabolism, the initial in vitro tests that can not take these features into account could eliminate a powerful drug that does not perform well in such simple systems. The drug could be metabolized to different compounds in animal models than in humans, which may also demonstrate different adsorption or distribution patterns. Or finally, compounds can look very promising all the way through clinical trials, but then demonstrate unpleasant side effects or a high degree of tolerance when used by the human population at large. It is never obvious which compound will continue to look promising as each stage of tests and development are initiated.

Control of tumorous growth has been achieved to a certain degree using oncolytic vinca alkaloids as antitumour agents alone or in combination with other antineoplastic drugs in cancer chemotherapy for more than 20 years. Approximately 30 alkaloids with a wide range of pharmacological activities have been extracted from the Vinca rosea (*Catharanthus roseus*), commonly known as the periwinkle plant. Of these, only vinleurosine, vinrosidine, vinblasline and vincristine possess significant antitumour activity. In particular, vinblastine and vincristine have been used widely as single agents and in combination with outer antineoplastic drugs in cancer chemotherapy. In addition to the naturally occurring alkaloids, some vinca alkaloid analogues have been synthesized by functional transformation or by semi-synthetic processs (R. J. Cersosimo, et. al., Pharmacotherapy 3:359–274, 1983; P. Mangency, et al., Org. Chem. 44:3765–3768, 1979; R. Maral, et al., Cancer Lett. 22:49–54, 1984).

Chemically, these vinca alkaloids have a dimeric asymmetric structure composed of 2 nuclei linked by a carbon-carbon bond; a dihydroindole nucleus (vindoline), which is the major alkaloid contained in the periwinkle, and the indole nucleus catharanthine (FIG. 1). The structural difference between vincristine and vinblastine exists at the R1 position while vinblastine and vindesine differ with regard to the R2 and R3 substituents.

The mode of action of the antineoplastic vinca alkaloids has yet to be completely understood. However, it has been established that the antitumour activity is directly related to the high binding affinity of these compounds for tubulin, the basic protein subunit of microtubules (R. A. Bender and B. Chabner, In: Chabner (ed) Pharmacol. Princ. of Cancer Treat., Saunders. Phil, Pa., p. 256, 1982; W. A. Creasey, In: Hahn (ed) Antibiotica, Vol. 2, Springer, Berlin, p. 414, 1979). The consensus is that these agents arrest cell mitosis at metaphase by preventing tubulin polymerization to form microtubules and by inducing depolymerization (R. J. Owellen and C. A. Hartke, Cancer Res., 36:1499–1504, 1976; R. H. Himes and R. N. Kersey, Cancer Res., 36:3798–3806, 1976; R. S. Camplejohn, Cell Tissue Kinet 13:327–332, 1980). As such, the vinca alkaloids are cell cycle-specific antimitotic agents, or spindle poisons. The binding affinity of the vinca alkaloids to tubulin correlates poorly with the relative ability of vincristine, vinblastine and vindesine to inhibit cell growth (R. S. Camplejohn, supra; P. J. Ferguson and C. E. Cass, Cancer Res., 45:5480–5488, 1985). The major difference in antitumour activity between these drugs appears, therefore, to relate to their retention in tumour tissue (P. Ferguson, supra; J. K. Horton et al., Biochem. Pharmacol. 37:3995–4000, 1988). In a similar vein, the different toxicity profiles of the vinca alkaloids seems related to tissue uptake and retention properties rather than to inherent tubulin binding affinty. For example, studies have demonstrated that vincristine is more potent than vinblastine or vindesine in blocking fast axoplasmic transport in nerve cells (S. Ochs and R. Worth, Proc. Am. Assoc. Cancer Res., 16:70, 1975; S. Y. Chan et al., J. Neurobiol. 11:251–264, 1980). In addition, it is taken up into nerves 4 times faster than the other drugs (Z. Iqbal and S. Ochs, J. Neurobiol., 11:251–264, 1980) and exhibits an extended terminal elimination phase of plasma clearance, suggesting a more prolonged exposure to vincristine than to the other vinca alkaloids (R. L. Nelson et al., Cancer Treat. Rev., 7:17–24, 1980).

The in vitro and in vivo differences observed between the vinca alkaloids are striking given the subtle chemical alterations displayed by the various agents relative to their large, complex molecular structure. For example, vincristine is very effective in treating human rhabdosarcomas transplanted in nude mice whereas vinblastine is not active in this system (N. Bruchovsky et al., Cancer Res. 25:1232–1238, 1965). This difference is obtained simply as a result of the substitution of an aldehyde group for a methyl group at the R1 position. Further, this chemical substitution leads to a shift in the toxicology profile such that peripheral neuropathy (in the absence of hematological toxicity) is dose limiting in humans for vincristine whereas anemia and leucopenia are typically dose limiting for vinblastine (W. P. Brads, Proc. Int. Vincaalkaloid Symposium, 95–123, 1980; S. S. Legha, Med. Toxicol., 1:421–427, 1986). A particularly interesting therapeutic profile has been observed for a new semisynthetic vinca alkaloid named navelbine (vinorelbine, 5'-noranhydroblastine). This compound is less potent than vinbiastine and vincristine against murine P388 and L1210 leukemia but is active against cells derived from human lung cancer whereas the other vinca alkaloids are inactive (S. Cros, et al., Seminars in Oncology, 16:15–20, 1989). As well, clinical trials on navelbine support its utility in treating non-small cell lung cancer (A. Depierre et al., Am. J. Clin. Oncol., 14:155–119, 1991; A. Yokoyama et al., Am. Soc. Clin. Oncol., 11:957, 1992). The toxicity profile of this agent appears similar to that of vinblastine, where hematological toxicities and not neurological side effects are dose limiting.

Vincristine has proved particularly useful as an intravenously administered oncolytic agent in combination with other oncolytic agents for the treatment of various cancers including central- nervous-system leukemia, Hodgkin's disease, lymphosarcoma, reticulum-cell sarcoma, rhabdomyosarcoma, neuroblastoma, and Wilm's tumor. It is for intravenous use only and the intratecal administration is uniformly fatal. Following single weekly doses, the most common adverse reaction is hair loss; the most troublesome are neuromuscular in origin. When single weekly doses of the drug are employed, the adverse reactions of leukopenia, neuritic pain, constipation, and difficulty in walking can occur. Other adverse reactions that have been reported are abdominal cramps, ataxia, foot drop, weight loss, optic atrophy with blindness, transient cortical blindness, fever, cranial nerve manifestations, parehesia and numbness of the digits, polyuria, dysuria, oral ulceration, headache, vomiting, diarrhea, and intestinal necrosis and/or perforation.

Navelbine (vinorelbine tartrate) is a novel vinca alkaloid in which the catheranthine unit is the site of structural modification. It's antitumour activity is also thought to be due primarily to its ability to interfere with microtubule activity thereby inhibiting mitosis at metaphase through its interaction with tubulin. It is indicated in the treatment of advanced non-small cell lung cancer as a single agent or in combination, administered by intravenous route only. Its side effects include phlebitia or extravasion injury as it is a moderate vasicant. Studies on adverse reactions based on use of Navelbine as a single agent indicate Granculocytopenia to as the major dose-limiting toxicity, although it was generally reversible and not cumulative over time. Mild to moderate peripheral neuropathy manifested by pareathesia and hypesthesia are the most frequently reported neurologic toxicities, occurring in 10% of patients. Mild to moderate nausea occurs in roughly one-third of patients treated with Navelbine with a slightly lesser fraction experiencing constipation, vomiting, diarrhea, anorexia, and stomatitis.

Compounds exhibiting lessened toxic effects with equal or greater chemotherapeutic activity remain to be achieved. Thus, a need remains for a drug providing improved antitumour efficacy for the treatment of cancer.

It is, therefore, an object of the present invention to provide a method of treating cancer which comprises administering to a human patient suffering from cancer and in need of treatment, an amount of AHVB, effective to arrest or significantly slow the progress of the disease.

It is another object of the present invention to provide a method of using AHVB as an antitumour agent, comprising therapeutic amount of the chemical substance of the present invention to arrest tumorous growth.

The above and various other objects and advantages of the present invention are achieved by administration of a derivative of vinblastine, AHVB. Other objects and advantages will become evident from the following detailed description of the present invention.

SUMMARY OF INVENTION

The present invention is particularly directed to the use of a derivative of vinblastine, 3',4'-anhydrovinblastine (AHVB), which differs from vinblastine in that it possesses a double bond at the 3',4' position of the caranthine nucleus rather than the hydroxyl group that is present in the parent structure, as an antineoplastic agent in the therapeutic treatment of cancer.

The present invention is particulary directed to the new use of a derivative of vinblastine, 3', 4'-anhydrovinblastine (AHVB), which differs from vinblastine in that it possesses a double bond at the 3',4' position of the caranthine nucleus rather than the hydroxyl group that is present in the parent structure, as an antineoplastic agent in the therapeutic treatment of cancer.

One embodiment of the present invention involves the use of 3',4'-anhydrovinblastine, or variants therof, as an antineoplastic agent in the treatment of cancer.

Another embodiment of the present invention involves the use of 3',4'-anhydrovinblastine as an antineoplastic agent in the treatment of cancer, wherein the concentration of 3',4'-anhydrovinblastine is at significantly higher maximum concentration than therapeutically acceptable concentrations for vinblastine or navelbine for use in the treatment of cancer.

TABLES AND FIGURES

Table 1 shows relative cytotoxicity of vincristine, AHVB and navelbine on tumor cell lines.

Table 2 depicts estimates of subacutely toxic dosages of vincristine sulfate, navelbine, and AHVB when administered to healthy male Nb rats as a single, intraperitoneal injection.

FIG. 1 depicts the chemical structure of some vinca alkaloids.

FIG. 2 depicts comparison of effects of administering a single intraperitoneal injection, at a subacutely toxic dose, of vincristine, navelbine and AHVB to Nb rats bearing single well-developed, subcutaneous Nb2-U17 tumor transplants on average tumor weight and average weight of the rat as a function of time.

FIG. 3 depicts comparison of the effects of administering a single intraperitoneal injection, at a half subacutely toxic dose of vincristine, navelbine and AHVB to Nb rats bearing single well-developed, subcutaneous Nb2-U17 tumor transplants on average tumor weight and average weight of the rat as a function of time.

FIG. 4 depicts changes in mean animal weight of BDF1 mice bearing intraperitoneal P388 tumours following i.v. administration of saline, vincristine, navelbine and AHVB.

FIG. 5 depicts an example cytotoxicity curve used to estimate the $IC_{50}$ of various vica alkaloids.

FIG. 6 depicts P388 antitumor activity of selected formulations of vinca alkaloids.

FIG. 7 depicts a dose response curve obtained for AHVB when used to treat BDF1 mice bearing P388 tumors.

DETAILED DESCRIPTION OF THE INVENTION

Figure 8:
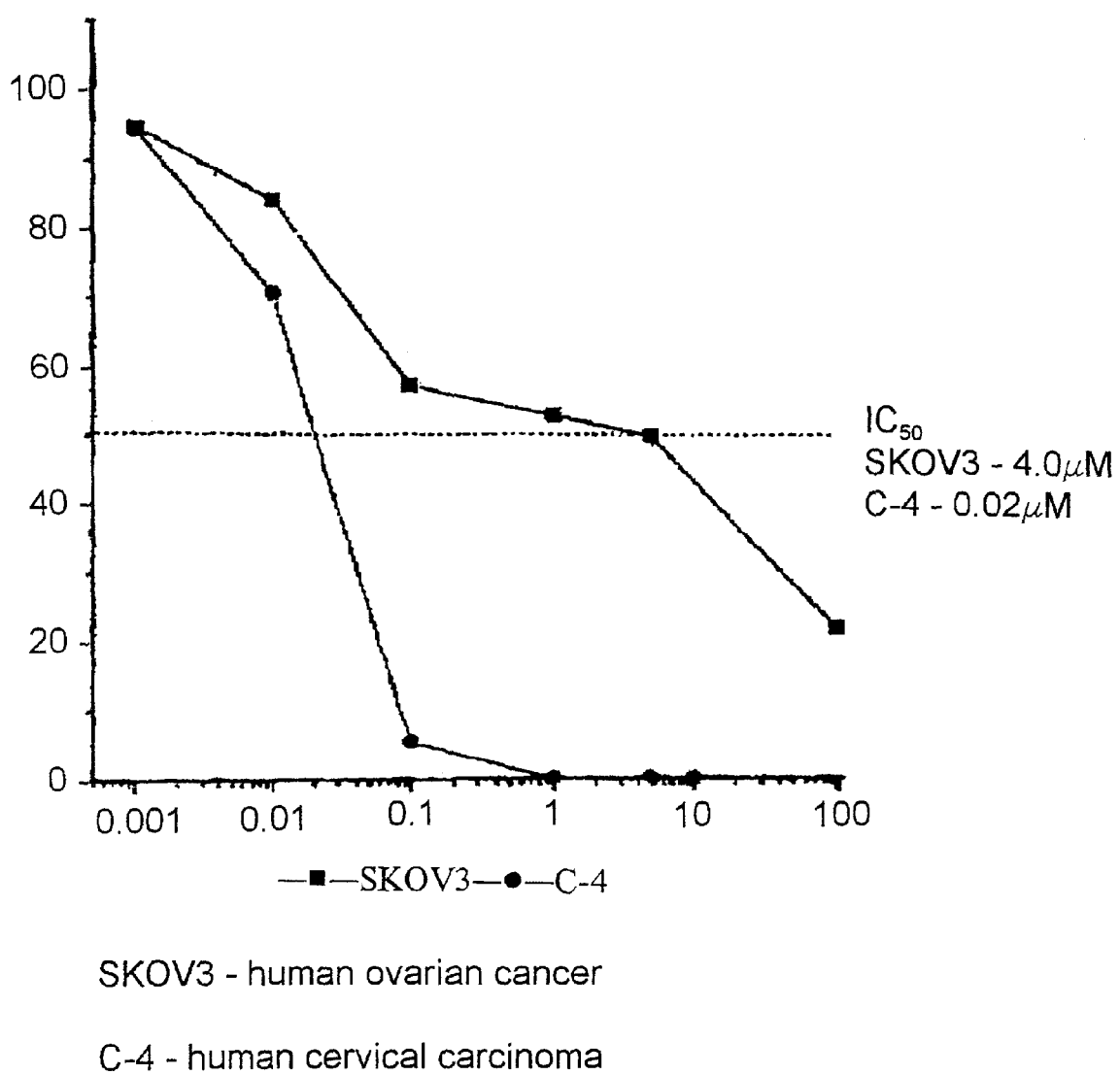
FIG. 8 depicts cytotoxicity curves used to estimate the $IC_{50}$ of AHVB on the cell lines SKOV3 and C-4.

There are many possible derivatives or variations of vinblastine possible. However, there is no certainty, even to those skilled in the area of anticancer drug development, that any such derivatives will be as efficacious or even more efficacious than the parent compound. This takes much testing and experimentation.

The term "variants" for purposes of 3',4'-anhydrovinblastine means any chemical structure that is a derivative of 3',4'-anhydrovinblastine achieved through conservative substitution of side groups, yet still exhibits the same or similar antineoplastic properties as 3',4'-anhydrovinblastine.

Characterization of AHVB Antitumour Activity In Vitro

Cytotoxicity experiments on AHVB were performed as direct comparisons with vincristine and navelbine in order to assess its inherent antineoplastic profile against a variety of tumour cell types relative to other relevant vinca alkaloids. The cytotoxicity of AHVB was investigated in vitro against a panel of tumour cell lines of varying lineage in order to determine the specificity of its antitumour activity with respect to cell type. The tumour lines studied were P388 lymphocytic leukemia (a murine lymphocytic leukemia), Noble (Nb) rat U17 lymphoma, MCF7 human breast carcinoma, H460 human non-small cell lung carcinoma, K562 human erythrokeukemia and LS180 human colon carcinoma based on established NCI in vitro new anticancer drug cytotoxicity screening protocols.

Standard dose response cytotoxicity assays (R. Mosmass, J. Immunol. Meth., 65:55–64, 1983) were utilized to determine the IC50 (drug concentration required to induce 50% inhibition of tumour cell growth) for vincristine, navelbine and AHVB. The results are presented in Table 1. The indicated cell lines were obtained from either the ATCC or NCI tumor repository and were cultured in tissue culture media by standard techniques well known to those skilled in the art, prior to dilution to a defined cell concentration required for the studies in 96 well plates.

A wide range of drug concentrations were exposed to tumour cells growing at log phase in 96- well microtitre plates. Cell concentrations depended on the cell line as well as the length of time to be cultured. Typically, P388 cells were plated at a concentration of 30,000, 2,000 and 750 cells per well for studies lasting 1, 3 and 7 days, respectively MCF7 cells were plated at a concentration of 7,000 and 1,500 cells per well for studies lasting 3 and 7 days, respectively. H460 cells were plated at a concentration of 2,500 and 1,000 cells per well for studies lasting 3 and 7 days, respectively. K562 cells were plated at a concentration of 1,500 and 10,000 cells per well for studies lasting 1 and 3 days, respectively. LS180 cells were plated at a concentration of 5,000 and 20,00 cells per well for studies lasting 3 and 7 days, respectively. After plating all cell lines were incubated (CO2 incubator at 37° C., 5% CO2) for 24 hours prior to addition of the cytotoxic agent (See Table 1). Subsequently the plates were incubated for the indicated time period. At specified times, cells were washed and subsequently exposed to the dye inclusion marker MTT (3-(4,5-dimethylthiazol-2-yl)-2,5diphenyl tetrazolium), which accumulated into viable cells. MTT was added to the cells at a final concentration of 50 $\mu$g per well. After a 4 hour incubation, the cells were washed free of media and unreacted MTT, prior to addition of DMSO which was required to solubilize the insoluble formazan precipitate that formed in viable cells. After the sample was mixed through repeated pipetting, the colored product was measured using a plate reader operating at 570 nm. The absorbance values obtained for cells cultured in the absence of drug was assumed to represent 100% viability. Experiments were repeated to substantiate any differences noted between DHVB and other vinca alkaloids.

Characterization of AHVB Antitumour Activity in Vivo

Evaluation of in vitro cell cytotoxicity was followed by studies regarding the antineoplastic activities of AHVB in two in vivo rodent models. Thus, anti-tumour activity of AHVB was determined using a rat solid tumour model (U17 lymphoma) and the murine P388 tumour model (R. Noble, et al., Cancer Res., 37:1455–1460, 1977; P. W. Gout et al., Biochem Cell Biol., 64:659–666, 1986).

The U17 cell line was originally derived from a transplantable malignant lymphoma that arose spontaneously in male Noble rats (British Columbia Cancer Research center Joint Animal Breeding Facility with parents obtained from the National Institutes of Health, Bethesda, Md.). The cell line is prolactin dependent and can readily be cultured in vitro. U17 derived solid tumours are generated by subcutaneous injection (via the trocar method) of a small (2 mm$^2$) piece of tumour tissue obtained from male Noble rat. Tumour tissue used for the implants arose two weeks after injection of 5×10$^6$ U17 cells (from culture) subcutaneously in the nape of the neck. For assessing the anti-tumour activity of AHVB, tumour bearing animals (2–4 gm tumours) were given a single treatment of drug and tumour size was measured as a function of time following treatment. The anti-tumour activity was assessed at a series of different doses in order to determine the maximum therapeutic dose of AHVB. Comparative studies between vincristine, vinblastine and AHVB were performed.

For these studies anti-tumour activity was determined at the maximum therapeutic dose of each drug.

Antitumour studies in mice focused on the P388 leukemia model. This is a standard NCI model for evaluation of new anti-cancer agents and it has been demonstrated to be sensitive to treatment with vinca alkaloids. This is an ascitic tumour model that was generated by intraperitoneal inoculation of 1×10$^6$ P388 cells (derived from culture, with an original cell line obtained from the NCI tumour repository) in BDF1 mice (Charles Rivers). One day after tumour cell inoculation, mice were treated with a single intravenous injection of drug. Animal weight was monitored daily and tumour progression was measured as an increase in animal weight and through estimation of survival time. Therapy was described by a decrease in tumour progression and an increase in survival time relative to an untreated control group. Initial studies established the maximum therapeutic dose for AHVB. Subsequently comparative studies with vincristine and navelbine were initiated where animals were treated with each drug at the maximum therapeutic dose.

The Canadian Council on Animal Care Guidelines were strictly adhered to and all animal protocols employed were approved by the Animal Care Committees of UBC and the BCCA. Animals were evaluated twice daily for any signs of stress (tumour or drug related) and if an animal appeared to be suffering (excessive weight loss or gain, lethargy, scruffy coat, etc.) than the animal was terminated.

Identification of Maximum Tolerated Dose of AHVB

Range-finding acute (14 day), single dose toxicity studies were performed in healthy male Nb rats in order to determine the maximum tolerated dose of vincristine sulfate, navelbine and AHVB when administered as a single, intraperitoneal injection in these rodents (see Table 2). To this end, healthy non-tumor bearing male Nb rats (weight range 333–399 grams) were divided in groups of 3 animals. Each group was used to test one drug at one dosage. In a group, each animal received one intraperitoneal injection at a particular dose, as indicated in Table 2. The volumes within which the drugs were administered depended on the concentration of the drug solution (in saline) and the weight of the animals, and ranged from 0.1–1.0 ml. Saline was used as a control. The highest dose of each drug which allowed survival of all animals in a group (3 out of 3) was taken as the subacutely toxic dosage for the drug, i.e. 0.7 mg/kg for vincristine, 2.0 mg/kg for navelbine and 3.0 mg/kg for AHVB.

The health of the animals was assessed by daily weight measurements in addition to behavioral indications of stress. Animals continued to be monitored throughout the complete 14 day study period. Animals were euthanized in the event of signs of severe stress or weight loss in excess of 20%. All animals were necropsied at the end of the study period or at the time of premature euthanasia. Once weight loss in excess of 20% or premature animal death was noted at a dose level, the dose was decreased until the weight loss nadir was less than 20% and no premature animal deaths were observed.

Studies in the Rat U17 Lymphoma Model

Cultures of the non-metastatic, pre-T Nb2 lymphoma line originally developed at The University of British Columbia and designated Nb2-U17 (Anticancer Research 14:2485–2492, 1994), and are available from the British Columbia Cancer Research Center. Cells from exponentially growing Nb2-U17 suspension cultures were injected subcutaneously into methoxyflurane-anesthetized, mature male Nb rats (5 rats; 310–380 grams; $5 \times 10^6$ cells/rat in 1 ml of culture medium) at the nape of the neck using a 1.5" 20-gauge needle. At about 3 weeks, when the tumours reached a size of 4–7 cm (length+width), the animals were sacrificed and the tumours used for transplantation as described below.

A tumour from a rat was excised, minced and the tumour tissue was put into trocars (2", 13 gauge). The tissue samples were implanted subcutaneously in the nape of the neck of methoxyflurane-anesthetized male Nb rats (248–404 grams; 1 trocar per rat). This procedure was repeated 5 times to get a total of 60 tumour-bearing rats to be used for efficacy studies of the 3 drugs.

When the tumours were well established (1.5–2 weeks later), three separate groups of 20 rats, as closely matched as possible in terms of both tumour weight and rat weight, were selected for administration of the three test articles (i.e. one group for each test article).

Vincristine was administered to rats weighing 281–384 grams, bearing tumours weighing 6.3–16.3 grams. Navelbine was administered to rats weighing 274–389 grams bearing tumours weighing 9.1–23.3 grams. AHVB was administered to rats weighing 303–400 grams, bearing tumours weighing 7.9–25.9 grams. Tumour weights were estimated using the hemi-ellipsoid model (weight in grams= length×depth×$\pi$/6 in cm).

The oncolytic effects of each of the three drugs were assessed at a subacutely toxic dose, determined for each drug in preliminary studies using non-tumour-bearing, mature male Nb rats, i.e. 3.0, 2.0 and 0.7 mg/kg for ANVB, navelbine and vincristine, respectively as illustrated in FIG. 2. In addition, each drug was assessed at 50% and 25% of its subacutely toxic dose. Five tumour-bearing rats were used to evaluate the effect at each dose level. The drugs were administered intraperitoneally as a single bolus in a volume of 0.19–0.31 ml, as indicated by the weight of the animals. To this end, drug preparations were diluted to appropriate concentrations using sparged saline adjusted with acetic acid to pH 4.2. For each drug, a group of 5 control rats received an intraperitoneal injection of the equivalent amount of saline (pH 4.2). The tumour-bearing rats were organized in the following groups:

| Group | Drug/Saline | Dose (mg/kg) |
| --- | --- | --- |
| 1 | saline | — |
| 2 | AHVB | 3.0 |
| 3 | AHVB | 1.5 |
| 4 | AHVB | 0.75 |
| 5 | saline | — |
| 6 | navelbine | 2.0 |
| 7 | navelbine | 1.0 |
| 8 | navelbine | 0.5 |
| 9 | saline | — |
| 10 | vincristine | 0.7 |
| 11 | vincristine | 0.35 |
| 12 | vincristine | 0.175 |

Following administration of the test articles, the animals; weight and tumour size (using calipers) were determined daily until the tumour reached an estimated weight of 35 grams, or started to ulcerate, at which times the animals were sacrificed (by carbondioxide inhalation) and subjected to necropsy. Animals were also monitored at least daily for signs of stress for the full length of the study. Animals manifesting severe symptoms of stress (rapid weight loss, panting, hunched posture, scruffy coat) were also sacrificed and a necropsy performed.

Anhydrovinblastine Sulfate (3',4'-dehydrovinblastine) was obtained from the British Columbia Cancer Agency (BCCA), Investigational Drug Section. Vincristine Sulfate (Sulfate of 22-oxovincaleukoblastine) was obtained from David Bull Laboratories Ltd., Australia. Navelbine (vinorelbine tartrate: 3',4'-didehydro-4'-deoxy-C'-norvincaleukoblastine-di-L-tartrate) was purchased from Burroughs Wellcome Inc., Canada; 0.9% Sodium Chloride Injection USP, pH 4.2 was purchased from Baxter.

The methodology involving animals was approved by the BCCA's Institutional Animal Care Committee (IACC) at UBC prior to conducting the studies (Animal Care Certificate No. A94–1602). During the study the care, housing and use of animals was performed in accordance with the Canadian Council on Animal Care Guidelines.

The results of the efficacy studies are given in FIGS. 2–3. FIGS. 2–3 present averages of data from 5 or fewer animals.

The effect of administering a single intraperitoneal, subacutely toxic dose of AHVB, navelbine and vincristine on the size of single, well-established Nb2-U17 lymphoma transplants (average weight 10–13 grams) and the weight of the animals, as a function of time are demonstrated in FIG. 2. Whereas the tumours in the control animals continued to increase in size to an average weight of about 40 grams in 6 days, the tumours in the drug-treated animals in each case regressed to essential non-palpability within 5 days of drug administration. After day 10, recurrence of tumours in navelbine- and AHVB-treated animals occurred to about the same extent. In contrast, recurrence of tumours was not observed in vincristine-treated animals (not even on day 29). FIG. 2 also shows that the animals lost weight following drug administration. However, most of the weight was regained after about 17 days. As controls for each drug, Nb2-U17 tumor transplant-bearing rats injected with saline were used. For each of the six groups five animals were used. Vincristine sulfate (0.7 mg/kg) was administered in a volume of 0.20–0.23 ml to rats weighing 281–331 grams bearing tumors weighing 7.6–14.2 grams. Navelbine (2.0 mg/kg) was administered in a volume of 0.24–0.31 ml to rats weighing 297–389 grams bearing tumors weighing 11.5–13.7 grams. AHVB (3.0 mg/kg) was administered in a volume of 0.20–0.24 ml to rats weighing 314–374 grams bearing tumors weighing 8.2–14.2 grams. Vincristine sulfate controls: saline was administered in a volume of 0.21–0.26 ml to rats weighing 294–370 grams bearing tumors weighing 9.4–14.6 grams. Navelbine controls: saline was administered in a volume of 0.25–0.29 ml to rats weighing 310–365 grams bearing tumors weighing 9.5–18.2 grams. AHVB controls: saline was administered in a volume of 0.19–0.25 ml to rats weighing 303–400 grams bearing tumors weighing 7.9–16.6 grams. The efficacies of each drug were determined separately at three different dosages versus a control.

FIG. 3 shows the anti-tumour effects of the three drugs at 50% of their individual maximum tolerated doses. The data show that navelbine was less potent than AHVB which in turn was less potent than vincristine, Nb2-U17 tumor transplant-bearing rats injected with saline were used as controls. For each of the six groups five animals were use. Vincristine sulfate (0.35 mg/kg) was administered in a volume of 0.23–0.27 ml to rats weighing 327–384 grams bearing tumors weighing 6.4–13.4 grams. Navelbine (1.0 mg/kg) was administered in a volume of 0.24–0.28 ml to rats weighing 296–351 grams bearing tumors weighing 9.1–14.1 grams. AHVB (1.5 mg/kg) was administered in a volume of 0.20–0.23 ml to rats weighing 308–359 grams bearing tumors weighing 9.7–19.5 grams. Vincristine sulfate controls: saline was administered in a volume of 0.21–0.26 ml to rats weighing 294–370 grams bearing tumors weighing 9.4–14.6 grams Navelbine controls: saline was administered in a volume of 0.25–0.29 ml to rats weighing 310–365 grams bearing tumors weighing 9.5–18.2 grams. AHVB controls: saline was administered in a volume of 0.19–0.25 ml to rats weighing 303–400 grams bearing tumors weighing 7.9–16.6 grams. The efficacies of each drug were determined separately at three different dosages versus a control. In FIG. 3, results of the three drugs at equivalent, i.e. half subacutely toxic, dosages are compared. The controls in FIG. 3 are the same as in FIG. 2.

Studies in the Murine P388 Model

A cytotoxicity curve was generated to estimate the $IC_{50}$ of vincristine, navelbine and AHVB in the murine P388 cell line (see FIG. 5). In this study, P388 cells derived from an ascitic tumor grown in BDF1 were first separated from red cells employing Ficoll-Paque. Isolated while cells were washed twice then placed in serum containing tissue culture media ($1\times10_5$ cells per ml of RPMI 1640 supplemented with L-glutamine, penicillin, streptomycin and 10% fetal bovine serum) and cultured for 2 hours. All non adherent cells were collected and that cell population was defined as P388 cells and used for cytotoxicity assays 24 hours later. Cytotoxicity assays were performed as described in the notes to Table 1. The drug concentrations used are indicated on the X-axis. Vincristine is represented by the filled circles, navelbine by the filled triangles and AHVB by the filled squares, The in vivo antitumour activity of AHVB was compared to that of vincristine, navelbine in the BDF1-murine P388 model in the procedure as follows. P388 cells were derived from the ascities of previously injected female BDF1 mice (19–21 grams) P388 cells, from the NCI tumor repository were inoculated directly into mice. The cells arrive from NCI frozen in 1 ml aliquots. These samples were thawed rapidly at 37° C. and subsequently injected (within 1 hour) intraperitoneally into two mice, 0.5 ml per mouse. One week (7 days) after inoculation, the tumor cells were harvested by removing peritoneal fluid using a sterile syringe with a 22 gauge needle. The cells, pooled from two animals, were counted using a heamocytometer, diluted (RPMI media) to a concentration of $2\times10^6$ cells/ml and 0.5 ml was then re-injected into each of two BDF1 mice. Remaining cells were washed and placed into a DMSO containing media and frozen (in freezer packs that cool at a defined rate). This process was repeated weekly over a 2- week period. Cells used for anti-tumor studies were collected from the third passage to the 20th passage. After the 20th passage the cells were no longer used for experimental studies. Newly established cells were derived from the frozen cells prepared as described above.

Groups (five mice per group) of female BDFI mice (Charles Rivers, Canada) were injected (intraperitoneal) with $10^6$ P388 cells (as described above). One day after tumor cell inoculation, the mice were given a bolus intravenous injection of indicated drug via the lateral tail vein. Control groups were injected with saline. Free drug samples were prepared on the day of injection such that the final concentrations were sufficient to deliver the indicated drug dose in a volume of 200 µl. All dilutions were made using 0.9% Sodium Chloride Injection USP. The mice were briefly (less than 30 sec.) restrained during intravenous injections. Dilation of the vein was achieved by holding the animals under a heat lamp for a period of between five and ten minutes. Following administration of the test articles, animals were weighed daily for fourteen days and monitored for signs of stress twice daily for the first 14 days (once daily on weekends) and once daily for the remainder of the study. Severely distressed animals were terminated by CO2 asphyxiation and the time of death was recorded to occur on the following day. Although complete dose titrations were completed for each drug, the data shown in FIG. 6 is that obtained after administration of the free drugs at their maximum tolerated dose. This was 3, 40 and 40 mg/kg for vincristine, navelbine and AHVB, respectively.

FIG. 4 presents the results of a study demonstrating vinca alkaloid induced weight loss following a single intravenous injection of the indicated drug at the maximum tolerated dose (see FIG. 6). These data were obtained as part of the study detailed in FIG. 6. After treating mice (bearing the P388 tumor) with a single dose of the indicated drug, animals were examined twice daily for the first 14 days (once daily on weekends). Mean body weight was determined daily over this time period and the results are shown in FIG. 4. Weight gain in the control is an indication of tumor progression. Results indicate that AHVB, administered at 40 mg/kg, is the least toxic of the three drugs evaluated.

The dose response curve obtained for AHVB when used to treat BDF1 mice bearing P388 tumors is presented in FIG. 7. The studies were conducted as described for FIG. 6. The maximum tolerated dose of AHVB (40 mg/kg) as specified in these studies reflects a very acute (within 1 hour) toxic reaction that limits further dose excalatin for i.v. administration of AHVB. This contrasts the more prolonged toxicity observed for Navelbine at its maximum tolerated dose and suggests that an ability to circumvent the acute toxicity of AHVB could lead to significant increases in its maximum tolerated dose.

Based on observation of the in vitro drug screen studies, it is surprising that AHVB would perform well as an antineoplastic agent for use in cancer therapy. The in vitro tests indicate that AHVB is consistently 10 to 15 fold less active on per molar basis (Table 1 and FIG. 5) than vincristine and navelbine. These results suggest that AHVB would not perform well as an antitumor agent. However, in an efficacy study, also employing the P388 cell line (see FIG. 6), the antitumor activity of AHVB at the maximum tolerated dose (40 mg/kg, single i.v. injection) is significantly better than that observed for vincristine (administered at the maximum tolerated dose of the free drug of 3 mg/kg). Improved antitumor activity, in this case, is measured by the number of long term survivors (>60 days). It is important to stress that, for this example, AHVB is approximately 10 times less toxic (on a weight basis) than vincristine. Therefore, 10 times more drug can be given and it is at this dose that improvements were observed in the long term survival of animals with P388 tumors. When compared to Navelbine, the in vivo results are even more surprising as the maximum tolerated dose of the two drugs in animals bearing P388 tumors are about the same (40 mg/kg).

FIG. 8 shows the cytotoxicity of AVHB on SKOV3 cells and C-4 cells with a 3 day incubation. The $IC_{50}$s for the SKOV3 and C-4 cells were 4.0 µM and 0.02 µM respectively. Both cell lines were obtained from the ATCC and grown using standard growth techniques and medium as described above. The $IC_{50}S$ were determined through standard cytotoxicity assays described above, with each well containing approximately $10^4$ cells.

Taken together, the results presented here show that AHVB has significant and unique pharmacological properties in vivo that lead to significant improvements in in vivo antitumor efficacy relative to other vinca alkaloids such as vincristine and navelbine. These results are unique and new in that the in vivo activity of AHVB predicted it to be significantly less on the basis of in vitro cytotoxicity studies.

The present invention also provides pharmaceutical compositions containing a compounds as disclosed in the claims in combination with one or more pharmaceutically acceptable, inert or physiologically active, diluents or adjuvants. The compounds of the invention can be freeze dried and, if desired, combined with other pharmaceutically acceptable excipients to prepare formulations for administration. These compositions may be presented in any form appropriate for the administration route envisaged. The parenteral and the intravenous route are the preferential routes for administration.

3',4'-anhydrovinblastine may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising 3',4'-anhydrovinblastine and a pharmaceutically acceptable carrier. 3',4'-anhydrovinblastine may be present in association with one or more non-toxic pharmaceutically acceptable carriers and/or diluents and/or adjuvants and if desired other active ingredients. The pharmaceutical compositions containing 3',4'-anhydrovinblastine may be in a form suitable for oral use, for example, as tablets, troches, lozenges, aqueous or oily suspensions, dispersible powders or granules, emulsion hard or soft capsules, or syrups or elixirs.

Compositions intended of oral use may be prepared according to any known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain active materials in admixture with excipients suitable for the manufacture of aqueous suspensions. Such excipients are suspending agents, for example sodium carboxymethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyetylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents or one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oils phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulation according to known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

3',4'-anhydrovinblastine may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

3',4'-anhydrovinblastine may he administered parenterally in sterile medium. The drug, depending on the vehicle and concentration used, can either be suspended or dissolved in the vehicle. Advantageously, adjuvants such as local anaesthetics, preservatives and buffering agents can be dissolved in the vehicle.

For the compounds of this invention, the dose to be administered, whether a single dose, multiple dose, or a daily dose, will vary with the particular compound being used. Factors to consider when deciding upon a dose regimen include potency of the compound, route of administration, size of the recipient and the nature of the patient's condition.

The dosage to be administered is not subject to defined limits, but in will usually be an effective amount. It will usually be the equivalent, on a molar basis of the pharmacologically active free form produced from a dosage formulation upon the metabolic release of the active free drug to achieve its desired pharmacological and physiological effects.

An oncologist skilled in the art of cancer treatment will be able to ascertain, without undue experimentations, appropriate protocols for effective administration of the compounds of this present invention by referring to the earlier studies of vinblastine and its derivatives.

It is to be understood that the examples described above are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

TABLE 1

RELATIVE CYTOTOXICITY OF VINCRISTINE, AHVB AND NAVELBINE ON TUMOR CELL LINES

| CELL LINES | TYPE | EXPOSURE TIME (days) | DRUG $IC_{50}$ (nM) | | |
|---|---|---|---|---|---|
| | | | VINCRISTINE | NAVELBINE | AHVB |
| P388 | murine leukemia | 1 | 11.0 ± 3.6 | 20.0 ± 10.0 | 140.0 ± 53.0 |
| | | 3 | 1.0 ± 0.3 | 0.7 ± 0.3 | 15.0 ± 8.7 |
| | | 7 | 2.0 | 2.5 | 20.0 |
| MCF7 | human breast | 1 | N.D. | N.D. | N.D. |
| | | 3 | >2500 | >2500 | >2500 |
| | | 7 | 2.6 ± 1.6 | 2.6 ± 1.6 | 31.3 ± 12.4 |
| H460 | human lung | 1 | N.D. | N.D. | N.D. |
| | | 3 | 3.5 | 0.3 | 10.0 |
| | | 7 | 2.5 | >0.5 | 5.0 |
| K562 | human erythroleukemia | 1 | >50.0 | >50.0 | >50.0 |
| | | 3 | 1.5 ± 0.4 | 2.5 ± 2.2 | 18.8 ± 8.8 |
| | | 7 | N.D. | N.D. | N.D. |

TABLE 1-continued

RELATIVE CYTOTOXICITY OF VINCRISTINE, AHVB AND NAVELBINE ON TUMOR CELL LINES

| CELL LINES | TYPE | EXPOSURE TIME (days) | DRUG $IC_{50}$ (nM) | | |
|---|---|---|---|---|---|
| | | | VINCRISTINE | NAVELBINE | AHVB |
| LS180 | human colon | 1 | N.D. | N.D. | N.D. |
| | | 3 | >50.0 | >50.0 | >50.0 |
| | | 7 | 1.5 | 0.5 | 17.5 |

TABLE 2

Estimation of subacutely toxic dosages of vincristine sulfate, navelbine, and AHVB when administered to heathy male Nb rats as a single, intraperitoneal injection.

| Drug | Dose (mg/kg) | Mortality (surviving rats/injected rats) |
|---|---|---|
| 1 ml Saline pH 4.3 | n/a | 3/3 |
| Vincristine sulfate | [illegible] | [illegible] |
| | 0.7 | 3/3 |
| | [illegible] | [illegible] |
| | 0.5 | 3/3 |
| Navelbine (Vinorelbine tartrate) | [illegible] | [illegible] |
| | 5.0 | 0/3 |
| | [illegible] | [illegible] |
| | 2.0 | 3/3 |
| | [illegible] | [illegible] |
| Anhydrovinblastine | 10.0 | 0/3 |
| | [illegible] | [illegible] |
| | 4.4 | 0/1 |
| | [illegible] | [illegible] |
| | 3.0 | 3/3 |

We claim:

1. A method of treating lymphoma in a mammalian subject in need of such treatment which comprises administering, in a dose unit formulation, an antineoplastically effective amount of 3',4'-anhydrovinblastine.

2. The method of claim 1 wherein the dose unit formulation optionally includes pharmaceutically acceptable salts.

3. The method of claim 2, wherein the dose unit formulation additionally comprises a pharmaceutically acceptable carrier, diluent, excipient, adjuvant, vehicle or polymeric carrier.

4. The method of claim 2, wherein the antineoplastically effective amount of 3',4'-anhydrovinblastine is administered, enterally, parenterally or topically.

5. The method of claim 2, wherein the antineoplastically effective amount of 3',4'-anhydrovinblastine, is administered at a concentration that is approximately ten times the unit dose formulation of vinblastine that is therapeutically effective and appropriate for the weight and type of mammal.

6. A method of treating lymphoma in mammals which comprises administering, in a dose unit formulation, to a mammalian subject suffering from lymphoma and in need of treatment, an antineoplastically effective amount of 3',4'-anhydrovinblastine, optionally including pharmaceutically acceptable salts.

* * * * *